US00PP28668P2

(12) United States Plant Patent
Berk

(10) Patent No.: US PP28,668 P2
(45) Date of Patent: Nov. 21, 2017

(54) ***QUERCUS* TREE NAMED 'WOODSIDE SPLENDOR'**

(50) Latin Name: *Quercus palustris*
Varietal Denomination: Woodside Splendor

(71) Applicant: Paulus van den Berk, Sint-Oedenrode (NL)

(72) Inventor: Paulus van den Berk, Sint-Oedenrode (NL)

(73) Assignee: BOOMKWEKERIJ GEBR. VAN DEN BERK BV, Sint-Oedenrode (NL)

( * ) Notice: Subject to any disclaimer, the term of this patent is extended or adjusted under 35 U.S.C. 154(b) by 102 days.

(21) Appl. No.: 14/998,564

(22) Filed: Jan. 19, 2016

(51) Int. Cl.
*A01H 5/12* (2006.01)

(52) U.S. Cl.
USPC ..... Plt./225

(58) Field of Classification Search
USPC ..... Plt./225
See application file for complete search history.

(56) References Cited

PUBLICATIONS

UPOV his on 'Woodside Splendor', QZ PBR 2012/0872, filed Apr. 23, 2012.*

* cited by examiner

*Primary Examiner* — Anne Grunberg
(74) *Attorney, Agent, or Firm* — Penny J. Aguirre

(57) ABSTRACT

A new cultivar of *Quercus*, 'Woodside Splendor', that is characterized by its relatively narrow plant habit and its autumn foliage coloration that is deep red in color and appears early in the season and is retained for a long period of time.

2 Drawing Sheets

Botanical classification: *Quercus palustris.*
Variety denomination: 'Woodside Splendor'.

CROSS REFERENCE TO A RELATED APPLICATION

This application is related to a European plant breeders' rights application filed on Apr. 23, 2012, application No. 2012/0872. There have been no offers for sale anywhere in the world prior to the filing of this Application and no accessibility to one of ordinary skill in the art could have been derived from printed plant breeder's rights documents.

BACKGROUND OF THE INVENTION

The present invention relates to a new and distinct cultivar of *Quercus palustris*, and will be referred to hereafter by its cultivar name, 'Woodside Splendor'. 'Woodside Splendor' is a deciduous tree grown for use as a landscape plant.

The Inventors selected the new cultivar, 'Woodside Splendor', as a seedling in Sint-Oedenrode, Netherlands in the September of 1996. The seedbed had been planted with seeds collected from an unnamed and unpatented open pollinated plants of *Quercus palustris.*

Asexual reproduction of the new cultivar was first accomplished by grafting onto *Quercus palustris* by the Inventor in Sint-Oedenrode, Netherlands in September of 1996. Asexual propagation of 'Woodside Splendor' by grafting has shown that the unique features of the new cultivar are stable and are reproduced true to type in successive generations.

SUMMARY OF THE INVENTION

The following traits have been repeatedly observed and represent the characteristics of the new cultivar. These attributes in combination distinguish 'Woodside Splendor' as a new and unique cultivar of *Quercus.*

1. 'Woodside Splendor' exhibits a relatively narrow plant habit.
2. 'Woodside Splendor' exhibits autumn foliage coloration that is deep red in color and appears early in the season and is retained for a long period of time.

The parent of 'Woodside Splendor' differs from 'Woodside Splendor' in having a broader plant habit and in having autumn foliage coloration that appears later in the season, is lighter in color and not retained as late in the season. 'Woodside Splendor' can also be compared to *Quercus palustris* cultivars 'Pringreen' (U.S. Plant Pat. No. 9,093) and 'Helmonds Red Globe' (not patented). 'Pringreen' is similar to 'Woodside Splendor' in having an upright plant shape. 'Pringreen' differs from 'Woodside Splendor' in having a broader plant habit and in having autumn foliage coloration that appears later in the season, is lighter in color and not retained as late in the season. 'Helmonds Red Globe' is similar to 'Woodside Splendor' in having foliage with deep colored foliage in autumn that is retained late in the season. 'Helmonds Red Globe' differs from 'Woodside Splendor' in having a broader plant habit when mature and in having autumn foliage coloration that appears later in the season.

BRIEF DESCRIPTION OF THE DRAWINGS

The accompanying colored photographs illustrate the overall appearance and distinct characteristics of the new *Quercus*, 'Woodside Splendor'. The photographs were taken of a 19 year-old tree of 'Woodside Splendor' as grown outdoors in a trial plot in Sint-Oedenrode, Netherlands.

Figure 1:
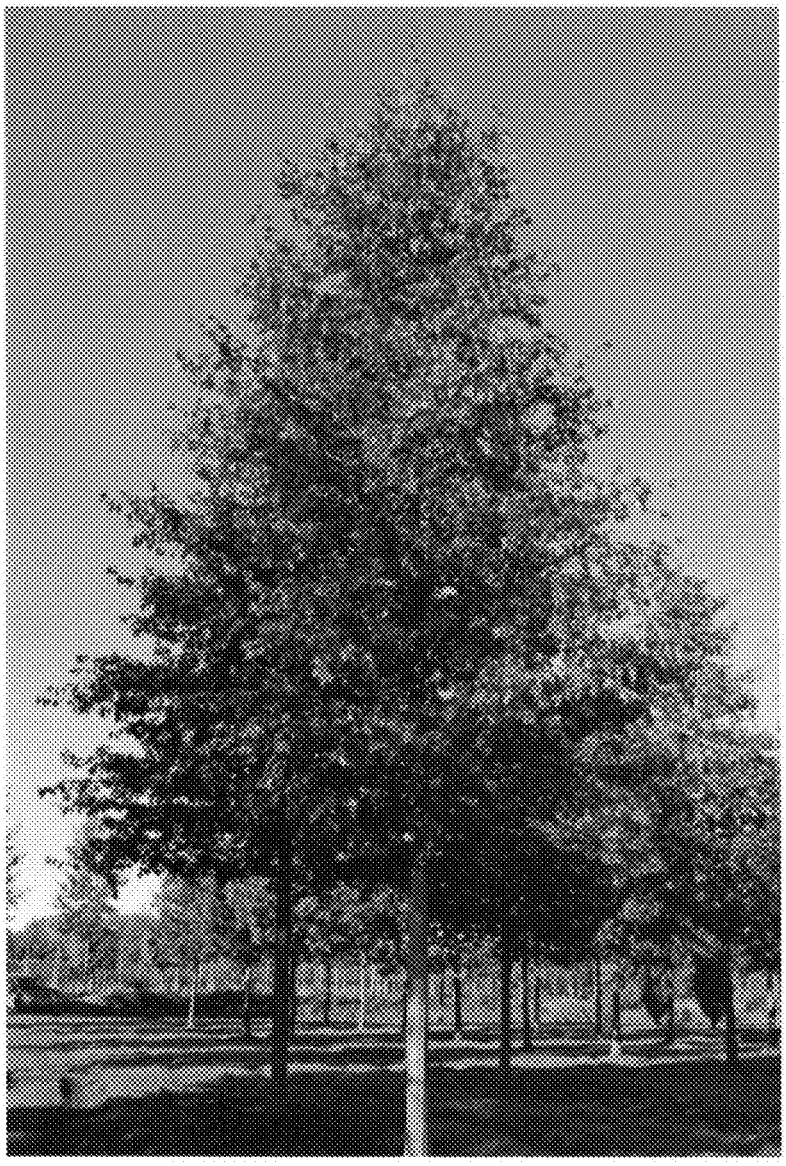
FIG. 1 provides an overall view of the foliage and plant habit of 'Woodside Splendor' in fall.
Figure 2:
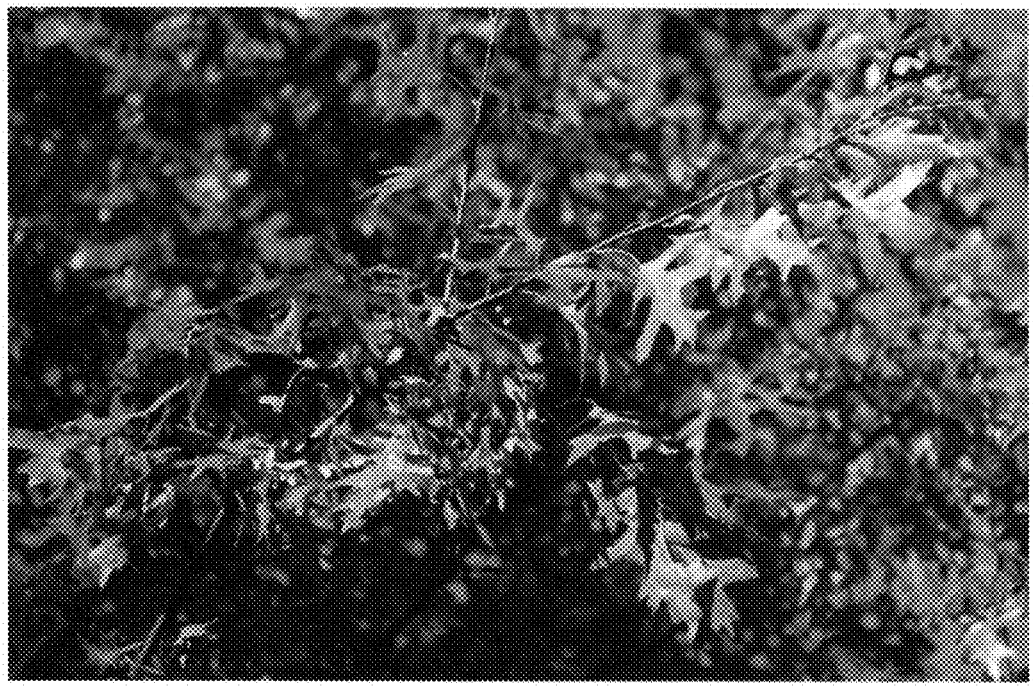

The photograph in FIG. 2 provides a close-up view of the fall foliage of 'Woodside Splendor'.

The colors in the photographs are as close as possible with the photographic and printing technology utilized and the color values cited in the Detailed Botanical Description accurately describe the colors of the new *Quercus*.

DETAILED BOTANICAL DESCRIPTION

The following is a detailed description of a 19-year old plant of the new cultivar as grown outdoors in a trial plot in Sint-Oedenrode, Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Plant type*.—Deciduous tree.

*Plant habit*.—Narrow pyramidal to pyramidal.

*Height and spread*.—An average of 9 m in height and 5 m in spread as a 19-year old plant in the landscape.

*Cold hardiness*.—At least to U.S.D.A. Zone 5.

*Diseases and pests*.—No particular resistance or susceptibility has been observed.

*Root description*.—Fibrous, freely branched.

*Propagation*.—Grafting.

*Growth rate*.—Moderately vigorous.

*Cropping time*.—Approximately 4 years from a graft to produce a young tree about 225 cm in height.

Branch description:

*Branch color*.—Young branches; upper side 175A, lower side 152A, with both surfaces later fading to 148A and covered with a very thin layer of 198A and 198B, mature branched and trunk; color between 197A and N199A.

*Branch size*.—Lateral branches; average of 130 cm in length and 8 mm in diameter, main stem in a average of 20 cm in diameter measured 10 cm from the soil level.

*Branch surface*.—Lateral and main trunk; glabrous and moderately glossy with lateral branches moderately to densely covered with lenticels; an average of 0.5 mm in length and 156C in color.

*Internode length*.—Average of 1.4 cm and 4 mm near apex of branches.

*Branch aspect*.—Held at an average angle of 80° to main trunk.

*Branch strength*.—Very strong.

*Branching*.—Freely branching, an average of 30 lateral branches, pinching is not required, but will improve branching.

Foliage description:

*Leaf shape*.—Pinnatisect, sinuses parallel to divergent.

*Leaf division*.—Simple.

*Leaf quantity*.—An average of 93 leaves per lateral branch.

*Leaf base*.—Very broad acute to nearly straight, often slightly unequal.

*Leaf apex*.—Leaf tip and tips of lobes narrow acute with mucronate outer tips.

*Leaf fragrance*.—None.

*Leaf venation*.—Pinnate, 144B on upper surface and 145C to 145D on lower surface.

*Leaf margins*.—Entire, except for a few large teeth, average of 1 per lobe.

*Leaf arrangement*.—Alternate.

*Leaf aspect*.—Held outward on pendant petioles held at about a 45° angle from branch.

*Leaf attachment*.—Petiolate.

*Leaf surface*.—Upper surface; very glossy, lower side moderately glossy and covered with small tufts of stellate hairs on vein axils; average of 1 mm in length and 164D in color.

*Leaf size*.—Up to 10.9 cm in length and 11 cm width.

*Leaf color*.—Young upper surface; between 143C and 144C, young lower surface; 146B to 146C, mature upper surface; between 143A and 144A, mature lower surface; 146A, autumn coloration; young and mature leaves upper and lower surface turn 175B to 175C, then turn between 45A and N45A.

*Petioles*.—Average of 3.8 cm in length and 1 mm in width, held at about a 45° angle and slightly pendant, color of upper and lower surface 151B.

*Stipules*.—None.

Inflorescence description: No flowers have been observed.

It is claimed:

1. A new and distinct cultivar of *Quercus* tree named 'Woodside Splendor' as herein illustrated and described.

* * * * *